United States Patent [19]  [11] Patent Number: 4,806,527
Christensen et al.  [45] Date of Patent: Feb. 21, 1989

[54] AVERMECTIN DERIVATIVES

[75] Inventors: Burton G. Christensen, Cliffside; Helmut Mrozik, Matawan; Michael H. Fisher, Ringoes, all of N.J.

[73] Assignee: Merck & Co., Inc., Rahway, N.J.

[21] Appl. No.: 26,409

[22] Filed: Mar. 16, 1987

[51] Int. Cl.⁴ .................. A61K 31/70; C07H 17/04; C07D 313/06

[52] U.S. Cl. .................. 514/30; 536/7.1; 549/264; 71/88

[58] Field of Search .................. 536/7.1; 549/264; 514/30; 71/88

[56] References Cited

U.S. PATENT DOCUMENTS 3,950,360  4/1976  Aoki et al.
4,171,314  10/1979  Chabala et al.
4,173,571  11/1979  Chabala et al.
4,203,979  5/1980  Fisher et al. .................. 536/7.1
4,310,519  1/1982  Albers-Schonberg et al.

FOREIGN PATENT DOCUMENTS 170006  2/1986  European Pat. Off.
2166436  5/1986  United Kingdom.

Primary Examiner—Johnnie R. Brown
Assistant Examiner—Elli Peselev
Attorney, Agent, or Firm—David L. Rose; Michael C. Sudol

[57] ABSTRACT

There are disclosed derivatives of avermectin compounds with a $\Delta26,27$-alkyl chain of 4, 5 or 6 members at the 25-position. The compounds are prepared from the known $\Delta26,27$-compounds by the appropriate synthetic procedures at the 5-, 8-, 9-, 13-, 22- and 23-positions. The compounds are potent antiparasitic agents, in particular, the compounds are anthelmintic, insecticidal and acaricidal agents.

9 Claims, No Drawings

AVERMECTIN DERIVATIVES

BACKGROUND OF THE INVENTION

Certain Δ26,27-alkyl compounds are known in the art. See European patent application EPO No. 170,006 and U.K. application No. 2,166,436. The instant compounds are derivatives of such compounds which contain new or modified substituents at the 13-, 22- and 23-positions. Further modifications are possible at the 5-, 8- and 9-positions.

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519 and are incorporated herein by reference. The avermectin compounds are a series of macrolides, each of which is substituted thereon at the 13-position with a 4'-(α-L-oleandrosyl)-α-L-oleandrose group. Avermectin compounds and the derivatives thereof of this invention have a very high degree of anthelmintic and antiparasitic activity.

Milbemycin compounds are similar to the above avermectin compounds in that the 16-membered macrocyclic ring is present. However, such compounds have no substitution at the 13-position and have a methyl or ethyl group at the 25-position (the position the $R_2$ group is found in the above structure). Such milbemycin compounds and the fermentation conditions used to prepare them are described in U.S. Pat. No. 3,950,360. In addition, 13-deoxy-avermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec-butyl rather than a methyl or ethyl group at the 25-position.

SUMMARY OF THE INVENTION

The instant invention is concerned with derivatives of avermectin compounds where various Δ26,27-alkyl compounds unsubstituted or with preexisting substitutions at the 13-, 22- and 23-positions are converted to other substituted derivatives at such positions and other reactions are carried out at the 5-, 8- and 9-positions. Thus, it is an object of this invention to describe such compounds. It is a further object of this invention to describe the processes useful for the preparation of such compounds. A still further object is to describe the use of such compounds as anthelmintic, insecticidal and acaricidal agents. Still further objects will become obvious from a reading of the following description.

DESCRIPTION OF THE INVENTION

The compounds of the instant invention are best realized in the following structural formula:

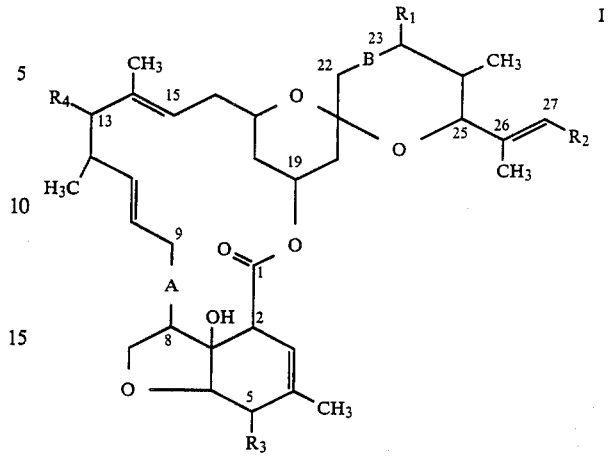

wherein
A is a double bond or an epoxide linkage at the 8, 9-position;
B indicates a single bond or a double bond at the 22,23-position;
$R_1$ is hydrogen, hydroxy, fluoro or ketone provided that $R_1$ is present only when B represents a single bond and $R_1$ is hydroxy only when $R_4$ is other than hydrogen;
$R_2$ is methyl, ethyl or isopropyl;
$R_3$ is hydroxy, loweralkoxy or loweralkanoyloxy; and
$R_4$ is hydrogen, hydroxy, loweralkoxy, loweralkanoyloxy, halogen,

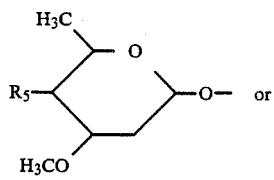 or

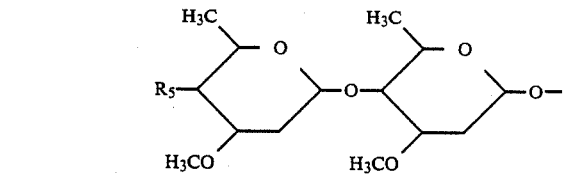

where $R_5$ is hydroxy, ketone, amino, loweralkylamino, diloweralkylamino, lower alkanoyl amino loweralkoxy, loweralkanoyloxy, loweralkoxycarbonyloxy, carbamoyloxy, N-loweralkylcarbamoyloxy or N,N-diloweralkylcarbamoyloxy.

Preferred compounds of the instant invention are realized in the foregoing structural formula wherein
A is a double bond or an epoxide linkage;
B is a single or a double bond;
$R_1$ is hydrogen, or hydroxy;
$R_2$ is methyl, ethyl or isopropyl;
$R_3$ is hydroxy or loweralkoxy; and
$R_4$ is hydrogen, hydroxy, halogen,

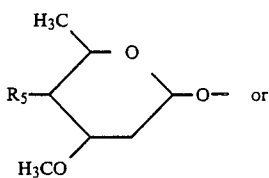

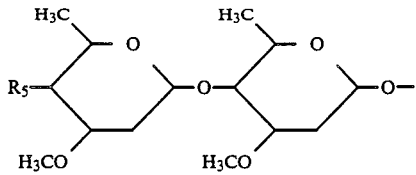

wherein R₅ is hydroxy, ketone, amino, loweralkylamino or diloweralkylamino.

The most preferred compounds are realized wherein
A is a double bond;
B is a single or a double bond;
R₁ is hydrogen;
R₂ is methyl, ethyl or isopropyl;
R₃ is hydroxy; and
R₄ is hydrogen or

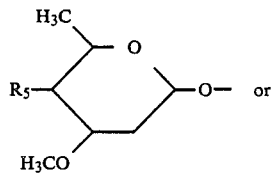

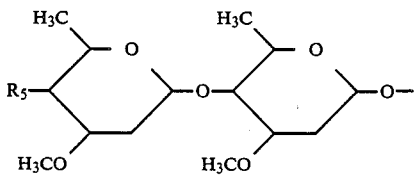

where R₅ is hydroxy, amino, or loweralkylamino. Preferred compounds of the instant invention are further realized in the following compounds.

26,27-Didehydro-13,23-dideoxyavermectin B2a aglycone 22,23,26,27-Tetradehydro-13,23-dideoxyavermectin B2a aglycone (or 26,27-bisdehydro-13-deoxyavermectin B1a aglycone)

26,27-Diedehydro-13,23-dideoxy-28-dimethyl-avermectin B2a aglycone 22,23,26,27-Tetradehydro-13,23-dideoxy-28-methylavermectin B2a aglycone (or 26,27-bisdehydro-13-deoxy-28-methylavermectin B1a aglycone)

26,27-Didehydro-13-deoxy-5,23-dioxoavermectin B2a aglycone 26,27-Didehydro-13-deoxy-5-oxoavermectin B1a aglycone (also named 22,23,26,27-tetradehydro-13,23-dideoxyavermectin B2a aglycone)

26,27-Didehydro-5-oxoavermectin B1a aglycone (also named 22,23,26,27-tetradehydro-23-deoxyavermectin B2a aglycone)

26,27-Didehydroavermectin B1a 26,27-Didehydro-5,13-dioxoavermectin B1a aglycone 26,27-Didehydroavermectin B1a aglycone 4''-Deoxy-4''-methylamino-26,27-didehydroavermectin B1a 26,27-Didehydro-22,23-dihydroavermectin B1a 26,27-Didehydro-13-deoxy-13-fluoro-avermectin B1a aglycone.

26,27-Didehydro-13,23-dideoxy-23-fluoroavermectin B2a aglycone 26,27-Didehydroavermectin B1a 8,9-oxide In the instant invention the term "loweralkyl" is intended to indicate those alkyl groups of from 1 to 6 carbon atoms such as methyl, ethyl, propyl, isopropyl, butyl, pentyl, hexyl and the like.

The term "loweralkoxy" is intended to include those alkoxy groups of from 1 to 6 carbon atoms such as methoxy, ethoxy, propoxy, isopropoxy, butoxy, pentoxy, hexoxy and the like.

The term "loweralkanoyl" is intended to include those alkanoyl groups of from 2 to 6 carbon atoms such as acetyl, propionyl, butyryl, pentanoyl, hexanoyl and the like.

The term "carbamoyl" is intended to include the amino carbonyl group (H₂NCO—).

The term "halogen" is intended to include the halogen atoms, fluorine, chlorine, bromine or iodine.

The above structural formula is shown without a definitive stereochemistry. However, during the course of the synthetic procedures used to prepare such compounds, the products of such procedures can be a mixture of stereoisomers. In particular, the stereoisomers at the 13- and 23-positions may be oriented either α- or β-representing such groups being below or above the general plane of the molecule respectively. In each such case both the α- and β-configurations are intended to be included within the ambit of this invention.

The starting materials for the instant compounds are among those disclosed in U.K. application No. 2,166,436 having the following structure:

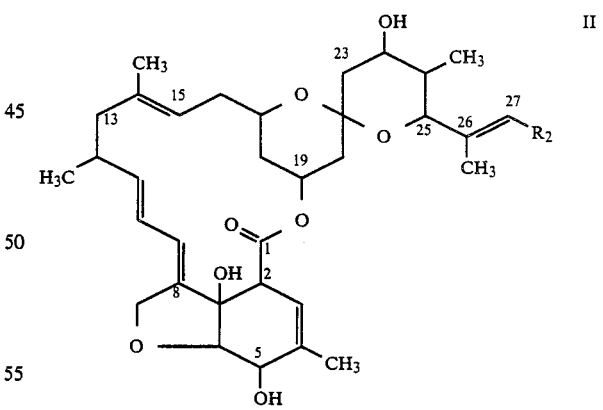

where R₂ is as defined above.

The reactions used to convert the above compounds to the compounds of the instant invention vary depending upon the particular position of the reaction or upon the particular substituent group being prepared.

The 23-hydroxy group of the above structure II can be removed to prepare the 23-unsubstituted compound, the 22,23-unsaturated compound or the 22,23-ketone, as shown in the following partial structural formula where only the 21- to 25-carbon atoms are shown:

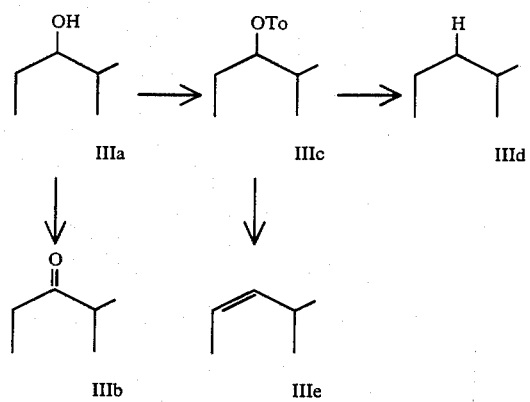

During the above procedures, and several other procedures described below, it is often useful to protect reactive hydroxy groups in order to ensure that the reaction takes place only at the desired position. Subsequent to the desired reaction or reactions, the protective group is removed. A very useful protective group is a trisubstituted silyl group, particularly the trialkyl silyl, most particularly the t-butyl-dimethylsilyl group. The protection is generally carried out at the 5-, 13-, 4'- and 4"-groups by combining the unprotected compound in an aprotic solvent such as methylene chloride, toluene, benzene, ethyl acetate, tetrahydrofuran, dimethylformamide and the like and adding the protecting reagent which is the silyl halide of the protecting group. The preferred reagent is tert-butyl-dimethylsilyl chloride. Also, in order to minimize side reactions, there is included in the reaction mixture a base to react with the acid halide released during the course of the reaction. Preferred amines are imidazole, pyridine or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours.

The protecting groups are removed by treatment with p-toluene sulfonic acid monohydrate in methanol at about room temperature for up to 2 hours.

Other protecting groups, such as various acyl groups are readily employed in the preparation and removal of such groups is well within the knowledge of those skilled in the art.

The avermectin 23-hydroxy compounds, IIIa, elsewhere suitably protected are converted to the 23-ketone compounds, IIIb, by oxidation. The 23-hydroxy group is oxidized to the 23keto group using oxidizing agents such as pyridinium dichromate; oxalylchloride-dimethylsulfoxide; acetic anhydride-dimethylsulfoxide; chronic acid-dimethylpyrazole; chromic acid; trifluoromethylacetic anhydride-dimethylsulfoxide; m-chlorosuccinimidate chromic acid-acetic acid; and the like. Oxalylchloride-dimethylsulfoxide is the preferred oxidizing agent. Suitably protected compounds, as described above, are employed. The reaction is carried out at from dry-ice bath temperatures to room temperature, preferably from dry-ice bath temperatures to 0° C. and is complete in from 1-24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chronic acid-dimethylpyrazole reactions, methylene chloride is preferred. The compounds are isolated from the reaction mixture using procedures known to those skilled in the art. See U.S. Pat. No. 4,289,760.

The 23-hydroxy compound, IIIa, can also be converted into the Δ22,23-compound IIIe or the 22,23-dihydro compound, IIId, via a thiocarbonyloxy (To) intermediate, IIIc.

The 23-hydroxy compound, IIIa, is reacted with an alkyl substituted phenoxy thiocarbonyl halide:

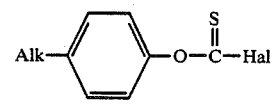

wherein Alk is loweralkyl and Hal is a halide. The reaction results in the substituted thiocarbonyloxy group at the 23-position, IIIc. The reaction is carried out in an aprotic solvent. In addition, the presence of a tertiary amine is recommended which may be used in excess to the exclusion of any other solvent. The reaction is completed in about ½ to 16 hours at room temperature with most reactions being completed in about 7 hours. The thiocarbonyl halide reagent is generally used in excess, preferably having from a 1 to 10 molar excess of such reagent. The preferred reagent for use in this reaction is the (4-methylphenoxy)thionocarbonyl chloride.

The Δ22,23-compounds IIIe are prepared in a thermal cis-elimination reaction of the thiocarbonyloxy leaving group carried out by heating the intermediate neat or in a high boiling solvent such as trichlorobenzene at about 150°–250° C. for from ½ to 3 hours. The products are isolated using techniques known to those skilled in the art.

The 23-deoxy compounds, IIId, are prepared by reduction of compound IIIc with tributyltin hydride in the presence of a free radical initiator. The reaction with the tributyltin hydride is carried out in an aprotic solvent such as toluene, at reflux or about 80°–110° C. and is complete in about 1-6 hours. The course of the reaction is monitored by techniques such as thin layer chromatography. If the reaction is seen to be incomplete, an additional amount of tributyltin hydride and free radical initiator is added, and the reaction heated for an additional 1-6 hours. The preferred free radical initiator is azobisisobutyronitrile, which is employed in catalytic amounts. Other free radical initiators may be employed such as ultraviolet light or heat. If ultraviolet light is employed, the reaction temperature may be lowered, however, thin layer chromatographic analysis may reveal the need for additional reaction times. If heat is used as the free radical initiator, additional reaction may also be required. The product is isolated using known techniques. See U.S. Pat. No. 4,328,335.

With respect to the substituents at the 5-position, it is noted that the starting materials have the hydroxy function present at such position. The 5-hydroxy group can be used to prepare other 5-alkoxy groups in addition to the methoxy group as well as 5-loweralkanoyloxy groups. The reaction involves alkylation or acylation of the 5-hydroxy. Further, it is described below that a hydroxy group or hydroxy-containing groups can be prepared at the 13-position. These groups can also be alkylated or acylated using the below described procedure.

The alkyl derivatives of the 5-0- and 13-0-positions, also referred to as the 5- and 13-alkoxy derivatives, and the hydroxy containing groups attached at the 13-position, referred to as the 4'- and 4"-positions of the mono- and di-saccharide substituents respectively, are prepared by the direct alkylation of the corresponding hydroxy group. The 5-position hydroxy is more reactive than the 13-, 4'- or 4"-hydroxy groups and generally no protection is required of such groups, during the preparation of 5-0-derivatives although it is usually necessary to protect the 23-hydroxy group. The 7-position hydroxy is very non-reactive and has no effect on these reactions.

To substitute an alkyl on the hydroxy groups, the appropriate starting material is treated with an alkyl halide in the presence of silver oxide ($Ag_2O$) catalyst. The preferred halide employed in this process is the iodide. The halide is used in excess quantity, and the reaction is carried out at from about room temperature to 70° C. The halide may be present in a single molar excess or greater, and may even be employed as the solvent for the reaction, dispensing with the solvents listed below. The reaction is preferably carried out in a solvent such as ether, tetrahydrofuran, acetonitrile, methylene chloride, glyme, dichloroethane, benzene and the like. The duration of the reaction varies with the position of substitution as well as the size of the group being substituted onto the substrate. The 4"-, 4'- and 13-positions require longer reaction times than the 5-position and larger alkyl groups require longer reaction times. Overall, the reaction times required for this reaction is between 1 and 100 hours. See U.S. Pat. No. 4,200,581.

The acyl derivatives, in particular the lower-alkanoyl derivatives of the 5, 13, 4' and 4" hydroxy groups are prepared using known acylation techniques. Again, the reactivity of the various hydroxy groups varies with the 5-position hydroxy being more reactive than the 13, 4' or 4" hydroxy groups and the 7-hydroxy being non-reactive. The 23-position is also reactive and must be protected if acylation is to be avoided. Often a mixture of acylated compounds is obtained which are readily separated using known separation techniques.

The acylation reagents generally employed are the loweralkanoyl halide, or the alkylhaloformate. Chlorine is the preferred halide. The anhydride is also a useful acylation reagent. Where the halide reagents are employed, it is often useful to include a non-reactive amine, such as a trisubstituted amine to neutralize the hydrogen halide liberated during the course of the reaction. The reaction is carried out in an aprotic solvent such as pyridine at from 0° to 100° C. for from 1 to 24 hours. The product is isolated and separated from other acylated products using techniques known to those skilled in the art. See U.S. Pat. No. 4,201,861.

The reactions at the 8,9-double bond involve converting it to an epoxide. The epoxide compounds are prepared by treating the appropriately substituted avermectin compound with a mild oxidizing agent. The oxidizing agent should be capable of preparing the epoxide from the 8,9-double bond, but not be so strong as to completely cleave the bond or to affect any of the other unsaturations or other functional groups present on the molecule. It has been found that oxidizing agents with such characteristics are exemplified by m-chloroperbenzoic acid, alkyl hydroperoxides catalyzed with vanadyl acetylacetonates, and the like.

The reaction is carried out in an inert solvent, not capable of being oxidized, such as methylene chloride, chloroform, and the like. In order to prevent the reaction from becoming too vigorous, it is carried out at moderate temperatures. Generally, room temperature is adequate although cooling to a temperature of about 0° C. is acceptable. The reaction is usually complete in a fairly short time, up to about 2 hours, at room temperature. The compounds of this invention are isolated using techniques known to those skilled in the art. Generally, a slight excess of the oxidizing agent is employed such as from about 10 to 30% excess, when it is desired to prepare the 8,9-epoxide. See U.S. Pat. No. 4,530,921.

The reactions at the 13-position involve converting the unsubstituted 13-position to a 13-hydroxy which can then be converted to the 13-alkoxy and 13-loweralkanoyloxy as is described above. Additionally, the α-L-oleandrosyl or α-L-oleandrosyloxy-α-L-oleandrosyl groups may be substituted on the 13-hydroxy. This will in turn provide for additional hydroxy groups which can be alkylated and acylated as described above.

The unsubstituted 13-position is converted to the 13-hydroxy. Avermectins have an oxygen substituent at the 13-position of the macrolide ring, which is missing in the milbemycins and a number of closely related microbial products such as the milbemycins disclosed in U.S. Pat. No. 3,950,360. A number of chemical procedures are available for the introduction of a C-13 hydroxy group to such 13-unsubstituted compounds. The C-13 position is an allylic position and is therefore activated for reactions having this regiospecificity. Allylic bromination with N-bromosuccinimide yields a 13-bromoderivative, which is then reacted with sodium acetate, sodium formate, sodiumphenoxyacetate and the like to give a C-13-position ester, which gives the desired C-13-hydroxy compound after ester hydrolysis. Allylic oxidation with selenium dioxide in the presence of a carboxylic acid also gives C-13-position carboxylic acid ester derivatives (EP-184-308-A), which yield C-13-hydroxy derivatives upon hydrolysis.

These C-13-hydroxy derivatives are valuable intermediates for further transformations. For instance reaction with 4-(4-O-tert-butyldimethylsilyl)alfa-L-oleandrosyl)-L-oleandrosylfluoride as described by K. C. Nicolaou et al. (J. Am. Chem. Soc. 106, 4189–4192 (1984)) introduce a disaccharide substituent. These glycoside derivatives are then deprotected to give highly useful products.

The 13-hydroxy group is readily glycosylated wit the mono- or di- α-L-oleandrosyl group using a variety of procedures.

The processes for the substitution of the carbohydrate groups onto the hydroxy groups of the substrate molecule involve the Koenigs-Knorr process, the silver triflate process or the orthoester process.

The carbohydrate starting materials employed for the Koenigs-Knorr, the Helferich modification thereof and the silver triflate processes are protected by acylating all of the free hydroxy groups. The preferred protecting group is the acetyl group, however, other groups such as the benzoate may be employed. The processes for the blocking of the hydroxy groups are well known to those skilled in the art. The acetyl blocking groups are also easily removed at the completion of the reaction by catalytic hydrolysis, preferably base-catalyzed hydrolysis such as with an alcoholic ammonia solution.

The Koenigs-Knorr and silver triflate processes use as starting materials acetohalosugars preferably the acetobromo sugars. The bromine atom is substituted on a carbon atom adjacent to an acetyl group and the sugar moiety becomes bonded to the substrate at the carbon atom to which the halogen was attached.

In the Koenigs-Knorr reaction the avermectin compound is dissolved under anhydrous conditions in an aprotic solvent. Ether is the preferred solvent, however, methylene chloride, acetonitrile, nitromethane, dimethoxy ethane and the like may also be employed. To the substrate solution is added the acetohalosugar and silver oxide. A single molar equivalent of the sugar is required for the reaction, however, an additional 10 to 15 moles occasionally aids the reactions. Additional molar excesses beyond 15 may be employed in difficult reactions, however, such very large excesses tend to make the isolation of the product more difficult. It has been found preferable to employ freshly prepared silver oxide for the reaction, since the material tends to lose some of its catalytic efficiency upon standing for prolonged periods. The silver oxide is prepared from silver nitrate using known procedures. The reaction may be carried out at from 10°-15° C., however, reaction at room temperature is preferred. The reaction generally requires from 2 to 10 days for completion. Reaction progress is monitored by taking aliquots from the reaction mixture and examining them with thin layer chromatographic techniques. Possible side reactions are avoided by carrying out the reaction in the dark, and this method is preferred. The product is isolated using techniques known to those skilled in the art.

In one modification of the Koenigs-Knorr reaction, known as the Helferich modification thereof, a mercuric halide, such as mercuric chloride or bromide, alone or in combination with mercuric oxide or mercuric cyanide is substituted for the silveroxide. The above described reaction conditions be employed except that nitromethane and benzene are the preferred solvents and reflux temperature is the preferred reaction temperature.

The silver triflate reaction uses the reagent silver triflate (silver trifluoromethyl sulfonate) and the acetohalosugar in the same solvents listed above, with ether being preferred. The silver triflate is best if highly purified and freshly prepared just prior to its use. Methods for the preparation of silver triflate are well known to those skilled in the art. All of the reactants are combined in the solvent and the reaction conducted at from 10° to 50° C. for from 2 to 48 hours. Generally, however, the reaction is complete in about 24 hours at room temperature. The progress of the reaction may be followed by thin layer chromatography techniques. Again the reaction is preferably carried out in the dark, and with absolutely dry reactants and equipment.

A single mole of the sugar is required, however, a single molar excess is often used to aid in the course of the reaction.

During the course of the reaction a mole of triflic acid (trifluoromethanesulfonic acid) is liberated. This is a very strong acid and a molar equivalent of a base is required to neutralize the acid. Preferred bases are nonnucleophilic bases such as tertiary amines, preferably triethylamine, diisopropylethylamine, diazabicycloundecane, diazabicyclononane and the like. Since triflic acid is such a strong acid, if the base used is not a strong enough base to neutralize all of the acid, the residual acid will adversely affect the course of the reaction and of the isolation of the product. The product is isolated using techniques known to those skilled in the art.

The orthoester process prepares sugar derivatives of the avermectin compounds from orthoesters of a lower alkanol and the sugar at the 13-hydroxy function of said avermectin compounds. The ortho-esters are prepared from the acetohalosugars using a loweralkanol and procedures which are well known to those skilled in the art. The reaction is carried out in an aprotic solvent such as dichloroethane, nitromethane, methylene chloride, dimethoxy ether, acetonitrile, tetrahydrofuran and the like. Dichloroethane, nitromethane, dimethoxy ethane and tetrahydrofuran are preferred. The reaction is preferably carried out at the reflux temperature of the reaction mixture and is generally complete in from about 4 to 24 hours. Catalytic amounts of mercuric bromide or mercuric chloride are added to aid in the reaction. During the course of the reaction one mole of the alcohol used to make the orthoester is liberated. Thus, the preferred method is azeotropically distill off the solvent to remove the alcohol and to force the reaction to completion. To prevent any volume reduction, fresh solvent is added as the distillation proceeds to maintain a constant volume. To isolate the product, the solvent is generally removed and the residue washed with a reagent to remove the mercury salts, such as aqueous potassium iodide. The product is then isolated using known techniques. See U.S. Pat. No. 4,203,976.

The monosaccharide and disaccharide compounds with hydroxy at the 4' or 4" positions may be converted to the 4' or 4" keto compounds and then to the 4' or 4" amino compounds.

In the first step, the avermectin starting materials are oxidized at the 4' or 4"-position to the corresponding keto compound. During the procedure the presence of any hydroxy groups at the 5 and 23-position will require that such hydroxy groups be protected in order that they too are not oxidized. The 7-hydroxy group is very unreactive and inert and need not be protected. The procedure used to prepare the protected intermediates are described above. The oxidation reaction is carried out in an inert solvent such as methylene chloride using oxalyl chloride or trifluoroacetic anhydride and dimethylsulfoxide as the oxidizing agent. Additionally, N-chlorosuccinimide and dimethylsulfide may be employed. The reaction proceeds by dissolving the oxalyl chloride or trifluoroacetic anhydride and dimethylsulfoxide (or other oxidizing reagents) in methylene chloride with cooling from $-50°$ to $-80°$ C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4' or 4"-keto compound is isolated using techniques known to those skilled in the art.

In the next step, the 4' or 4"-keto compound is aminated to prepare the unsubstituted amino compound ($R_5 = R_6 =$ hydrogen). The reaction is carried out in an inert solvent such as methanol at from $-25°$ to $+10°$ C. using ammonium salts and sodium cyanoborohydride as the aminating and reducing reagents. The reaction is complete in from 15 minutes to 2 hours and the product 4"-deoxy-4"-amino compound (or the corresponding 4' compound) is isolated using techniques known to those skilled in the art. Suitable ammonium salts are the acetate, propionate, benzoate and the like. The acetate is preferred.

As a variation to the foregoing amination reaction, alkyl ammonium salts could be used in place of the ammonium salts to prepare the mono alkyl substituted compounds directly. The same reagents, salts and reaction conditions as described above can be used for such a reaction.

The substitution reaction wherein the substituent is an acyl function is carried out using an acylating reagent in the presence of a base in an inert solvent. The preferred acylating reagents are loweralkanoyl anhydrides, loweralkanoyl halides, substituted benzene sulfonyl chlorides, lower alkyl sulfonyl chlorides, and the like. The reaction is carried out in an inert solvent such as methylene chloride in the presence of a non-reactive base such as pyridine or triethylamine in order to neutralize the acid produced during the course of the reaction. The reaction temperature is from $-10°$ to $25°$ C. and the reaction is complete in from 5 minutes to 1 hour. The product is isolated using known techniques.

The reaction for the preparation of the 4"-deoxy-4"-dialkylamino compounds (or the corresponding 4'-compound) is carried out using the alkylating reaction conditions of formaldehyde and a reducing agent such as sodium borohydride, in methanol. The reaction is carried out in aqueous medium using excess aqueous formaldehyde along with the presence of a small amount of acid such as acetic acid to facilitate the reaction. The reaction is carried out at from $-10°$ to $+10°$ C. with the solution of the 4"-deoxy-4"-amino-avermectin compound in methanol added dropwise over a period of from 30 to 60 minutes to the alkylating reagent mixture and the product is isolated using known techniques. See U.S. Pat. No. 4,427,663.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum attack primarily th intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of th infected host. The hydrogenated avermectin compounds of this invention have unexpectedly high activity against these parasites, and in addition are also active against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Gradually, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active monosaccharide or aglycone avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained wit our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one tha may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the individual avermectin components may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

5O-t-Butyldimethylsilyl-26,27-didehydro-13-deoxyavermectin B2a aglycone

A solution of 100 mg of compound LL-F28249-beta, 71 mg of imidazole and 78 mg of tert-butyldimethylsilyl chloride in 2.0 ml of anhydrous N,N-dimethylformamide is stirred at room temperature for 45 minutes. The reaction mixture is poured into 15 ml of water and the aqueous phase is extracted twice with 50 ml of methylene chloride. The organic phase is washed twice with water, dried with magnesium sulfate and concentrated in vacuo to a yellow oil. The crude product is purified by silica gel preparative layer chromatography with a methylene chloride:ethyl acetate-95:5 solvent system to give 5-O-t-butyldimethylsilyl-26,27-dehydro-13-deoxyavermectin B2a aglycone as an amorphous foam, which is characterized by 1H- and 13C-NMR spectra and by its mass spectrum.

EXAMPLE 2

5-O-t-Butyldimethylsilyl-26,27-didehydro-13-deoxy-23-O-(4-methylphenoxythiocarbonyl)avermectin B2a aglycone A solution of 28 mg of 5-O-t-butyldimethylsilyl-26,27-didehydro-13-deoxyavermectin B2a aglycone and 50 mg of 4-dimethylaminopyridine in 5.0 ml of pyridine is stirred in an ice bath under a blanket of nitrogen, while 0.5 ml of O-4-methylphenylchlorothioformate is added through a syringe. The ice bath is removed and the reaction mixture is stirred at room temperature for 7 hours. The reaction mixture is poured into 80 ml of ice water, 10 ml of saturated aqueous sodium chloride solution is added, and the product is extracted with three 75 ml portions of ether. The ether solution is washed with water and aqueous sodium chloride solution, dried, and concentrated in vacuo to a light oil. The crude product is purified on a silica gel column with methylene chloride containing from 0 to 10% of ethyl acetate as solvents. The product is obtained as a light foam, which is identified by $^1$H-, $^{13}$C-, and mass spectra as 5-O-t-butyldimethylsilyl-26,27-didehydro-13-deoxy-23-O-(4-methylphenoxythiocarbonyl) avermectin B2a aglycone.

EXAMPLE 3

5-O-t-Butyldimethylsilyl-26,27-didehydro-13,23-dideoxyavermectin B2a aglycone

A solution of 64 mg of 5-O-t-butyldimethylsilyl-26,27-didehydro-13-deoxy-23-O-(4-methylphenoxythiocarbonyl)avermectin B2a aglycone, 10 mg of 2,2'-azobis(2-methylpropionitrile) and 0.2 ml of tributyltin hydride in 5 ml of toluene is refluxed for 1 hour under nitrogen. It is then concentrated in high vacuum and the oily residue is taken up in about 1 ml of methylene chloride and transferred directly onto two 1 mm thick 20 by 20 cm silica gel plates for chromatographic purification with a hexane-ethyl acetate-75:25 solvent mixture. The major band is extracted with 10% methanol in ethyl acetate and concentrated in vacuo to a white foam, which is characterized by $^1$H-, $^{13}$C-, and mass spectra as 5-O-t-butyldimethylsilyl-26,27-didehydro-13,23-dideoxyavermectin B2a aglycone.

EXAMPLE 4

26,27-Didehydro-13,23-dideoxyavermectin B2a aglycone

A solution of 15 mg of 5-O-t-butyldimethylsilyl-26,27-didehydro-13,23-dideoxyavermectin B2a aglycone in 1.0 ml of methanol containing 10 mg of p-toluenesulfonic acid monohydrate is stirred at room temperature for 30 minutes, and then poured into a mixture of 0.5 ml of saturated aqueous sodium bicarbonate solution and 0.5 ml of water. The product is extracted with ether, dried with magnesium sulfate, concentrated in vacuo, and purified by silica gel preparative layer chromatography with a hexane-ethyl acetate-solvent mixture to give pure 26,27-didehydro-13,23-dideoxyavermectin B2a aglycone, which is characterized by its mass and $^1$H NMR spectra.

EXAMPLE 5

5-O-t-Butyldimethylsilyl-22,23,26,27-tetradehydro-13,23-dideoxyavermectin B2a aglycone A solution of 50 mg of 5-O-t-butyldimethylsilyl-26,27-didehydro-13-deoxy-23-O-(4-methylphenoxythiocarbonyl) avermectin B2a aglycone in 2.0 ml of 1,2,4-trichlorobenzene is heated under nitrogen in an oil bath of 200° C. for 2 hours. The reaction mixture is allowed to come to room temperature, diluted with methylene chloride, and the solution is purified on a column of 15 g of silica gel. After the trichlorobenzene is eluted with methylene chloride, the product is obtained with a methylene chloride:ethyl acetate-solvent mixture and characterized by mass and NMR spectra as 5-O-t-butyldimethylsilyl-22,23,26,27-tetradehydro-13,23-dideoxyavermectin B2a aglycone.

EXAMPLE 6

22,23, 26,27-Tetradehydro-13,23-dideoxyavermectin B2a aglycone

A solution of 25 mg of 5-O-t-butyldimethylsilyl-22,23,26,27-tetradehydro-13,23-dideoxyavermectin B2a aglycone in 2.5 ml of methanol containing 25 mg of p-toluenesulfonic acid monohydrate is reacted and purified as described in example 4 to give 22,23,26,27-tetradehydro-13,23-dideoxyavermectin B2a aglycone, which is characterized by its mass, $^1$H-, and $^{13}$C-NMR spectra.

EXAMPLE 7

26,27-Didehydro-13,23-dideoxy-28-dimethyl-avermectin B2a aglycone 26,27-Didehydro-13-deoxy-28-dimethyl-avermectin B2a aglycone (also identified as LL-F 28249 alpha) is reacted as described in examples 1,2,3, and 4 to give 26,27-didehydro-13,23-dideoxy-28-dimethyl-avermectin B2a aglycone.

EXAMPLE 8

26,27-Bisdehydro-13-deoxy-28-methylavermectin B1a aglycone 26,27-Didehydro-13-deoxy-28-methyl-avermectin B2a aglycone is reacted as described in examples 1, 2, 4 and 5, to give 26,27-bisdehydro-13-deoxy-28-methylavermectin B1a aglycone.

EXAMPLE 9

26,27-Didehydro-13-deoxy-5,23-dioxoavermectin B2a aglycone

To a solution containing 38.4 microliters of oxalyl chloride in 1.0 ml of dry methylene chloride at −60° C. is added 62 microliters of dry dimethylsulfoxide dissolved in 0.4 ml of dry methylene chloride, and the mixture is stirred at −60° C. for two minutes. Through a syringe a solution of 70 mg of 26,27-didehydro-13-deoxy-avermectin B2a aglycone (also identified as LL-F 28249 beta) in 1.2 ml of dry methylene chloride is added over a period of 5 minutes while maintaining the temperature at −60° C. The reaction mixture is stirred at this temperature for 30 minutes and 280 microliters of dry triethylamine are added. The mixture is stirred for 5 additional minutes at −60° C., the cooling bath is removed and the reaction mixture is allowed to come to ambient temperature. After addition of water the reaction product is extracted with methylene chloride, the extract is washed with water, dried and concentrated in vacuo to a light colored foam. Preparative silica gel layer chromatography with a methylene chloride:methanol solvent mixture gives pure 26,27-didehydro-13-deoxy-5,23-dioxo-avermectin B2a aglycone, which is identified by its mass and NMR spectra.

EXAMPLE 10

22,23,26,27-tetradehydro-13,23-dideoxyavermectin B2a aglycone

According to the procedure described in detail in Example 9, 140 mg of 22,23,26,27-tetradehydro-13,23-dideoxyavermectin B2a aglycone, which is obtained in example 6, are reacted in order to give 22,23,26,27-tetradehydro-13,23-dideoxyavermectin B2a aglycone.

EXAMPLE 11

26,27-Didehydro-5-oxoavermectin B1a aglycone

A solution of 2 g of 26,27-didehydro-13-deoxy-5-oxoavermectin B1a aglycone in 25 ml of formic acid is treated with 0.56 g selenium dioxide and stirred for 2 hours at 40° C. in accordance with the procedure published in EP-184-308-A. The crude reaction mixture is diluted with water and left standing in order to allow the formed formic acid esters to hydrolyze. The crude product is extracted with methylene chloride, dried and concentrated to a solid residue, which is further purified by silica gel chromatography and identified as 26,27-didehydro-5-oxoavermectin Bba aglycone by mass and NMR spectra.

EXAMPLE 12

26,27-Didehydro-4''-O-t-butyldimethylsilyl-5-oxoavermectin B1a

To a suspension of 12 mg of AgClO4, 11 mg of SnCl2, 100 mg of dried, crushed 4-A molecular sieves in 1 ml of dry ether stirred under argon at −15° C. is added 43 mg of 26,27-didehydro-5-oxoavermectin B1a aglycone (obtained in experiment 11) dissolved in 1.0 ml of ether. Addition of 24 mg of 4-O-(4'-O-t-butyldimethylsilyl-α-L-oleandrosyl)-αL-oleandrosyl-1-α-fluoride (prepared according to a procedure described by K. C. Nicolaou in J. Am. Chem. Soc. 1984, 106, 4189–4192), stirring at 0° C. for 16 hours and workup by dilution with ether, filtration through Celite, washing the filtrate with saturated sodium bicarbonate, brine, drying and evaporation to a glass gives the crude product. This is purified by preparative layer silica gel chromatography to give 26,27-didehydro-4''-O-t-butyl-dimethylsilyl-5-oxoavermectin B1a, which is identified by its characteristic mass and NMR spectra.

EXAMPLE 13

26,27-Didehydro-4''-O-t-butyldimethylsilylavermectin B1a

A solution of 310 mg of 26,27-didehydro-4''-O-t-butyldimethylsilyl-5-oxoavermectin B1a in 3.0 ml of methanol at −15° C. is treated with 25 mg of sodium borohydride and stirred 20 min at 25° C. The reaction mixture is treated with an ice-water mixture and the amorphous solid precipitate is obtained by filtration. The solid is washed with water and immediately purified by preparative layer silica gel chromatography to give 26,27-didehydro-4''-O-t-butyldimethylsilylavermectin B1a, which is identified by its mass and NMR spectra.

EXAMPLE 14

26,27-Didehydroavermectin B1a

A solution of 25 mg of 26,27-didehydro-4''-O-t-butyl-dimethylsilylavermectin B1a in 1.0 ml of tetrahydrofuran is treated with 3.0 ml of a solution prepared from 14 ml of anhydrous tetrahydrofuran, 4.0 ml of anhydrous pyridine, and 2.0 ml of a hydrogen fluoride solution in pyridine (commercial preparation consisting of about 70% of HF and 30% of pyridine supplied by Aldrich Chemical Company) for 24 hours at room temperature. Then the reaction mixture is poured onto an ice-water mixture, extracted with ether, washed with dilute aqueous sodium bicarbonate and water, dried, and concentrated in vacuo to a solid residue. Purification via preparative layer silica gel chromatography gives 26,27-didehydroavermectin B1a, which is characterized by its mass and NMR spectra.

EXAMPLE 15

26,27-Didehydro-5,13-dioxoavermectin B1a aglycone

To a solution containing 38.4 microliters of oxalyl chloride in 1.0 ml of dry methylene chloride at −60° C. is added 62 microliters of dry dimethylsulfoxide dissolved in 0.4 ml of dry methylene chloride, and the mixture is stirred at −60° C. for two minutes. Through a syringe a solution of 116 mg of 26,27-didehydro-5-oxoavermectin B1a aglycone in 1.2 ml of dry methylene chloride is added over a period of 5 minutes while maintaining the temperature at −60° C. The reaction mixture is stirred at this temperature for 30 minutes when 280 microliter of dry triethylamine is added. The mixture is stirred for 5 additional minutes at −60° C., and then the cooling bath is removed and the reaction mixture is allowed to come to ambient temperature. After addition of water the reaction product is extracted with methylene chloride, the extract is washed with water, dried and concentrated in vacuo to a light colored foam. Preparative layer silica gel chromatography with a methylene chloride:ethyl acetate solvent mixture gives pure 26,27-didehydro-5,13-dioxoavermectin B1a aglycone.

EXAMPLE 16

26,27-Didehydroavermectin B1a aglycone

A solution of 163 mg of 26,27-didehydro-5,13-dioxoavermectin B1a aglycone in 6.0 ml of ethanol at −15° C. is treated with 12.5 mg of sodium borohydride and stirred 20 min at 18° C. Then 35 ml of 0.1N aqueous acetic acid is added and the white precipitate is filtered and washed with water. The solid is dissolved in ethyl acetate and concentrated in vacuo. Purification by preparative layer silica gel chromatography gives 26,27-didehydro-avermectin B1a aglycone, which is identified by its mass and NMR spectra.

EXAMPLE 17

5-O-t-Butyldimethylsilyl-26,27-didehydroavermectin B1a aglycone

To a solution of 3.0 g of 26,27-didehydroavermectin B1a aglycone and 2.3 g of imidazole in 66 ml of N,N-dimethylformamide is added in one portion 2.55 g of tert-butyldimethylsilyl chloride. The reaction mixture is stirred at 18° C. for 60 minutes. The mixture is poured onto 300 ml of cold water and extracted three times with 100 ml portions of ether. The extracts are combined, washed repeatedly with water, dried and concentrated in vacuo to a yellow foam. The crude product is identified by TLC, HPLC, mass and NMR spectra as 5-O-t-butyldimethylsilyl-26,27-didehydroavermectin B1a aglycone, which is sufficiently pure for further reactions, or is purified in small batches by preparative layer silica gel chromatography.

EXAMPLE 18

26,27-Didehydro-4'',5-di-O-t-butyldimethylsilylavermectin B1a

If 52 mg of 5-O-t-butyldimethylsilyl-26,27-didehydroavermectin B1a aglycone is reacted exactly as described in example 12 one obtains 26,27-didehydro-4'',5-di-O-t-butyldimethylsilylavermectin B1a.

EXAMPLE 19

26,27-Didehydroavermectin B1a

A solution of 22 mg of 26,27-didehydro-4'',5-di-O-t-butyldimethylsilylavermectin B1a in 2.0 ml of tetrahydrofuran is cooled to 0° C. After addition of 0.44 microliters of a 1 molar solution of n-Bu$_4$NF in tetrahydrofuran the mixture is held at 0° C. for 16 hours. The reaction mixture is poured on a dilute aqueous solution of sodium bicarbonate, and the product is extracted with methylene chloride, the extract washed with water, dried and concentrated to a small volume under a stream of nitrogen. The concentrate is purified by preparative layer silica gel chromatography and identified by mass and NMR spectra as 26,27-didehydroavermectin B1a.

EXAMPLE 20

5-O-t-Butyldimethylsilyl-26,27-didehydroavermectin B1a

A solution of 130 mg of 26,27-didehydroavermectin B1a, 68 mg of imidazole, and 61 mg of tert-butyldimethylsilyl chloride in 1.5 ml of DMF is stirred at room temperature for 45 min. The reaction mixture is then poured into water. The product is extracted with ether; the extract is washed with water, dried and concentrated in vacuo to a light foam. Purification by preparative silica gel thin layer chromatography with CH2Cl2-EtOAc 85:15 solvent mixture gives 5-O-t-butyldimethylsilyl-26,27-didehydroavermectin B1a, which is characterized by NMR and mass spectra.

EXAMPLE 21

5-O-t-Butyldimethylsilyl-26,27-didehydro-4''-oxoavermectin B1a

A solution of 57 mg, 0.04 ml of oxalyl chloride in 1 ml of methylene chloride is stirred under nitrogen at −60° C. To this is added a solution of 70 mg, 0.065 ml of dimethylsulfoxide in 0.4 ml of methylene chloride, followed by a solution of 200 mg of 5-O-t-butyldimethylsilyl-26,27-didehydroavermectin B1a in 1.2 ml of methylene chloride. It is stirred at −60° C. for 30 min. Then 0.3 ml of triethylamine is added. After 5 minutes the reaction mixture is allowed to warm up to room temperature during the next hour. Then the mixture is poured into water and extracted with ether. The extract is washed with water, dried, and concentrated in vacuo to a yellow foam. The 5-O-t-butyldimethylsilyl-26,27-didehydro-4''-oxoavermectin B1a is identified by NMR and mass spectra and used without further purification as starting material for chemical reactions.

EXAMPLE 22

4''-Deoxy-4''-methylamino-5-O-t-butyldimethylsilyl-26,27-didehydroavermectin B1a A solution of 200 mg of 5-O-t-butyldimethylsilyl-26,27-didehydro-4''-oxoavermectin B1a and 190 mg of CH3NHOAc in 3 ml of MeOH is stirred at room temperature for 15 minutes. Then 12 mg of NaCNBH3 is added. After 1 hour the reaction mixture is poured into aqueous diluted sodium carbonate solution. The product is extracted with EtOAc, and the extract is washed with water, dried, and concentrated in vacuo to a yellow foam. The product is purified by preparative silica gel layer chromatography with a methylene chloride-MeOH 93:7 solvent mixture, and is identified by NMR and mass spectra as 4''-deoxy-4''-methylamino-5-O-t-butyldimethylsilyl-26,27-didehydroavermectin B1a.

EXAMPLE 23

4''-Deoxy-4''-methylamino-26,27-didehydroavermectin B1a.

A solution of 100 mg of 4''-deoxy-4''-methylamino-5-O-t-butyldimethylsilyl-26,27-didehydroavermectin B1a and 100 mg of p-toluenesulfonic acid monohydrate in 10 ml of MeOH is stirred at room temperature for 30 minutes, and then poured into dilute aqueous sodium bicarbonate solution. The product is extracted with EtOAc, washed with water and dried over magnesium sulfate, concentrated in vacuo, and purified by silica gel preparative layer chromatography with a methylene chloride-methanol 95:5 solvent mixture. It is identified by NMR and mass spectra as 4''-deoxy-4''-methylamino-26,27-didehydroavermectin B1a.

EXAMPLE 24

26,27-Didehydro-22,23-dihydroavermectin B1a

A solution of 265 mg of 26,27-didehydroavermectin B1a and 100 mg of triphenyl phosphine rhodium chloride (Wilkinson's homogeneous hydrogenation catalyst) in 16 ml of benzene is shaken at 18° C. in a hydrogen atmosphere of 15 pounds pressure until the uptake of one equivalent of hydrogen is completed. Evaporation of the solvent in vacuo and purification of the residue by preparative silicagel layer chromatography with methylene chloride-tetrahydrofuran-ethanol 94.5:5:0.5 solvent gives 26,27-didehydro-22,23-dihydroavermectin B1a, which is identified by its NMR and mass spectra.

EXAMPLE 25

5-O-t-Butyldimethylsilyl-26,27-didehydro-13-deoxy-13-fluoro-avermectin B1a aglycone A solution of 66 mg (50 μl) of diethylaminosulfur trifluoride in 2 ml of methylene chloride is stirred under nitrogen in a dry ice/acetone bath at −70° C. To this a solution of 250 mg of 5-O-t-butyldimethylsilyl-26,27-didehydroavermectin B1a aglycone in 2.5 ml of methylene chloride is added and the mixture is stirred 30 min at −70° C., then at −20° C. for 60 min, allowed to come to room temperature and poured into dilute aqueous sodium bicarbonate solution. The product is extracted with ether, washed with water, dried and concentrated in vacuo. Further purification by preparative silica gel layer chromatography with hexane-ethyl acetate 85:15 solvent mixture gives a mixture of two C-13-epimeric fluorides. A small amount of this mixture can be separated by repeated careful preparative silica gel TLC to give the two pure 5-O-t-butyldimethylsilyl-26,27-didehydro-13-deoxy-13-alpha and beta-fluoro-avermectin B1A aglycones, which are identified by NMR and mass spectra.

EXAMPLE 26

26,27-Didehydro-13-deoxy-13-fluoro-avermectin B1a aglycone

A solution of 30 mg of 5-O-t-butyldimethylsilyl-26,27-didehydro-13-deoxy-13-fluoro-avermectin B1a aglycone and 20 mg of p-toluenesulfonic acid monohydrate in 2.0 ml of MeOH is kept at room temperature for 30 minutes. It is then poured onto dilute aqueous sodium bicarbonate solution. The product is extracted with ether, washed with water, dried and concentrated in vacuo to a light foam. Purification by preparative TLC on silica gel with a methylene chloride-ethyl acetate 85:15 solvent mixture gives 26,27-didehydro-13-deoxy-13-fluoro-avermectin B1a aglycone, which is characterized by NMR and mass spectra.

EXAMPLE 27

5-O-t-Butyldimethylsilyl-26,27-didehydro-13,23-dideoxy-23-fluoroavermectin B2a aglycone A solution of 100 mg of 5-O-t-butyldimethylsilyl-26,27-didehydro-13-deoxyavermectin B2a aglycone in 4.5 ml of methylene chloride is stirred under N2 in a dry ice/acetone bath. To this a solution of 30 microL of diethyl amino sulfur trifluoride in 1.5 ml of methylene chloride is added. The reaction mixture is stirred at −70° C. for 30 minutes, then allowed to reach room temperature slowly over 90 minutes. Then the mixture is added to dilute aqueous sodium bicarbonate, and the product is extracted with ether, washed with water, and dried. After evaporation of the solvent in vacuo, the product is purified by preparative TLC and identified by NMR and mass spectra as 5-O-t-butyldimethylsilyl-26,27-didehydro-13,23-dideoxy-23-fluoroavermectin B2a aglycone.

EXAMPLE 28

26,27-Didehydro-13,23-dideoxy-23-fluoroavermectin B2a aglycone

A solution of 5-O-t-butyldimethylsilyl-26,27-didehydro-13,23-dideoxy-13,23-dideoxy-23-fluoroavermectin B2a aglycone in methanol is treated with p-toluenesulfonic acid monohydrate as described in example 4 to give 26,27-didehydro-13,23-dideoxy-23-fluoroavermectin B2a aglycone.

EXAMPLE 29

26,27-Didehydroavermectin B1a 8,9-oxide

A solution of 135 mg of 26,27-didehydroavermectin B1a and 6 mg of vanadium(III) acetylacetonate in dry methylene chloride is treated with a solution of 71 μl of a 3.0 molar solution of tert-butyl hydroperoxide and left at room temperature for 22 hours. Then the reaction mixture is poured into aqueous dilute sodium bicarbonate, and the product extracted with methylene chloride. The extract is washed with aqueous sodium bicarbonate solution and water, dried and evaporated in vacuo. Purification of the residue by preparative TLC on silica gel gives 26,27-didehydroavermectin B1a 8,9-oxide, which is characterized by NMR and mass spectral data.

What is claimed is:

1. A compound having the formula:

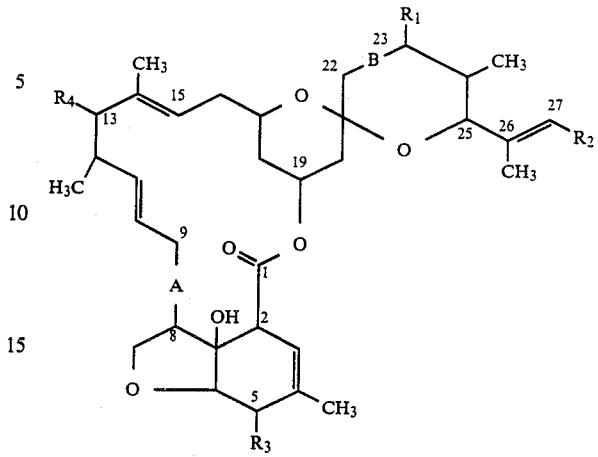

wherein
A is a double bond or an epoxide linkage at the 8,9-position;
B indicates a single bond or a double bond at the 22,23-position;
$R_1$ is hydrogen, hydroxy, fluoro or ketone provided that $R_1$ is present only when B represents a single bond;
$R_2$ is methyl, ethyl or isopropyl;
$R_3$ is hydroxy, loweralkoxy or loweralkanoyloxy; and
$R_4$ is hydroxy, loweralkoxy, loweralkanoyloxy,

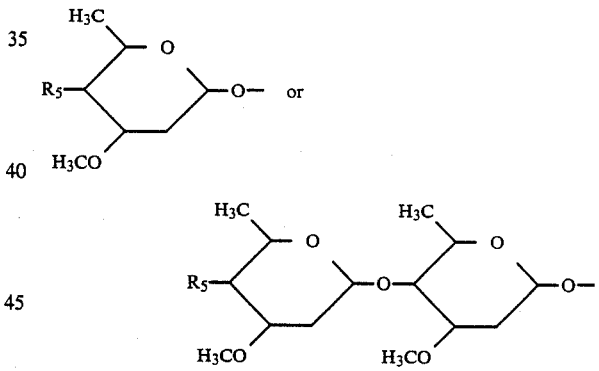

where $R_5$ is hydroxy, ketone, amino, loweralkylamino, diloweralkylamino, lower alkanoylamino loweralkoxy, loweralkanoyloxy, loweralkoxycarbonyloxy, carbamoyloxy, N-loweralkylcarbamoyloxy or N,N-diloweralkylcarbamoyloxy.

2. The compound of claim 1 wherein:
A is a double bond or an epoxide linkage;
B is a single or double bond;
$R_1$ is hydrogen, or hydroxy;
$R_2$ is methyl, ethyl or isopropyl;
$R_3$ is hydroxy or loweralkoxy; and
$R_4$ is hydroxy,

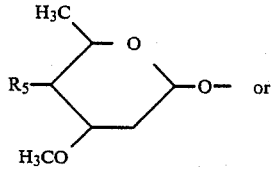

-continued

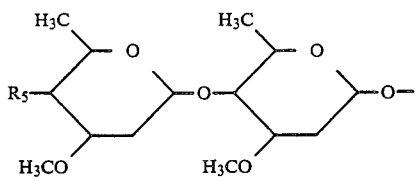

wherein R₅ is hydroxy, ketone, amino, loweralkylamino or diloweralkylamino.

3. The compound of claim 2 wherein:
A is a double bond;
B is a single or double bond;
R₁ is hydrogen;
R₂ is methyl, ethyl or isopropyl;
R₃ is hydroxy; and
R₄ is

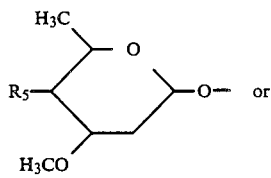 or

-continued

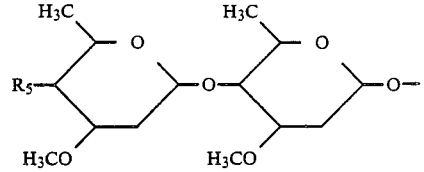

where R₅ is hydroxy, amino or loweralkylamino.

4. The compound of claim 1 which is: 26,27-Didehydro-22,23-dihydroavermectin B1a.

5. The compound of claim 1 which is: 26,27-Didehydroavermectin B1a.

6. The compound of claim 1 which is: 4″-Deoxy-4″-methylamino-26,27-didehydroavermectin B1a.

7. A composition useful for the treatment of parasite, helminth, insect, acarid or pest infections which comprises an inert carrier and an effective amount of a compound of claim 1.

8. A method for the treatment of parasite, helminth, insect, acarid and pest infections of an animal host which comprises administering to such animal hosts infected with such parasite, helminth, insect, acarid or pest infections, an effective amount of a compound of claim 1.

9. A method for the treatment of parasite, insect and pest infections of plants which comprises administering or applying to such plants or the soil in which they grow, an effective amount of a compound of claim 1.

* * * * *